United States Patent [19]
Slack et al.

[11] Patent Number: 5,905,151
[45] Date of Patent: May 18, 1999

[54] TRIMER CATALYST FOR ALIPHATIC AND AROMATIC ISOCYANATES

[75] Inventors: William E. Slack, Moundsville; Hersel T. Kemp, II, New Martinsville, both of W. Va.

[73] Assignee: Bayer Corporation, Pittsburgh, Pa.

[21] Appl. No.: 08/018,830

[22] Filed: Feb. 18, 1993

[51] Int. Cl.$^6$ ..................... C07D 251/34; C07D 263/00; C07D 263/16
[52] U.S. Cl. .................. 544/222; 528/49; 528/57; 528/85; 544/193; 560/330; 560/336; 560/355; 560/358; 560/359; 560/360
[58] Field of Search ................ 528/49, 57, 85; 544/193, 222; 560/330, 336, 355, 358, 359, 360

[56] References Cited

U.S. PATENT DOCUMENTS

| | | | |
|---|---|---|---|
| 3,635,848 | 1/1972 | Rambosek | 528/48 |
| 3,860,565 | 1/1975 | Barber, Jr. | 528/57 |
| 3,954,684 | 5/1976 | Farrissey, Jr. et al. | 252/426 |
| 4,080,345 | 3/1978 | Riemhofer | 528/57 |
| 4,126,741 | 11/1978 | Carleton et al. | 528/57 |
| 4,126,742 | 11/1978 | Carleton et al. | 528/67 |
| 4,263,408 | 4/1981 | Meyborg et al. | 528/57 |
| 4,379,905 | 4/1983 | Stemmler et al. | 528/73 |
| 4,412,073 | 10/1983 | Robin | 544/193 |
| 4,487,928 | 12/1984 | Richter et al. | 544/193 |
| 4,540,781 | 9/1985 | Barsa | 544/222 |
| 4,604,418 | 8/1986 | Shindo et al. | 524/296 |
| 4,632,785 | 12/1986 | Barsa | 560/146 |
| 5,248,703 | 9/1993 | Krueger et al. | 521/125 |
| 5,258,416 | 11/1993 | Krueger et al. | 521/125 |
| 5,453,455 | 9/1995 | Krueger et al. | 521/125 |

*Primary Examiner*—Rabon Sergent
*Attorney, Agent, or Firm*—Joseph C. Gil; N. Denise Brown

[57] ABSTRACT

This invention relates to a process for trimerizing organic polyisocyanates in the presence of thermally active catalyst systems. The catalyst systems comprise (a) compounds selected from the group consisting of 1) lithium salts of aliphatic or aromatic carboxylic acids, 2) lithium salts of hydroxyl group containing compounds wherein the hydroxyl groups are directed attached to an aromatic ring, and 3) lithium hydroxide; used in conjunction with (b) an organic compound which contains at least one hydroxyl group.

6 Claims, No Drawings

TRIMER CATALYST FOR ALIPHATIC AND AROMATIC ISOCYANATES

BACKGROUND OF THE INVENTION

This invention relates to a process for the trimerization of isocyanates in the presence of a thermally active catalyst. The catalyst system comprises A) a lithium compound selected from the group consisting of 1) lithium salts of aliphatic or aromatic mono- or dicarboxylic acids, 2) lithium salts of hydroxyl group containing compounds having from 1 to 3 hydroxyl groups per compound, wherein the hydroxyl groups are directly attached to an aromatic ring, and 3) lithium hydroxide; used in conjunction with B) an organic compound containing at least one hydroxyl group.

The trimerization of isocyanates to form polyisocyanurates is well known in the art. Trimerization catalysts described in the prior art include alkali carboxylates as described in DE-OS 3,219,608, basic alkali metal salts complexed with acyclic organic compounds as described in U.S. Pat. No. 4,379,905, basic alkali metal salts complexed with crown ethers as described in U.S. Pat. No. 4,487,928, and combinations of tertiary amines with specific quaternary ammonium salts as described in U.S. Pat. No. 3,954,684.

Catalysts described in U.S. Pat. Nos. 4,632,785 and 4,540,781 comprise alkali metal salts or quaternary ammonium salts of carboxylic acids of the formulas

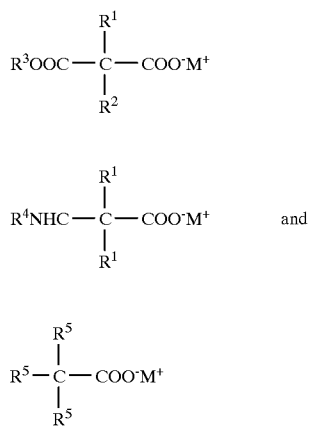

wherein $R^1$ is alkyl having from 2 to 8 carbon atoms, $R^2$ is a highly branched alkyl having from 3 to 8 carbon atoms, $R^3$ is selected from the group consisting of hydrogen, alkyl, and aryl, $R^4$ is selected from the group consisting of alkyl, aryl, aralkyl, and cycloalkyl, $R^5$ is independently selected from aryl, and $M^+$ is a cation selected from the group consisting of alkali metal cations and quaternary ammonium cations of a specific formula.

DESCRIPTION OF THE INVENTION

This invention relates to a new process for the preparation of a polyisocyanate having isocyanurate structure.

In particular, the process for the preparation of a polyisocyanate having isocyanurate structure comprises heating an organic isocyanate, or mixtures thereof, to a temperature of from about 100 to about 300° C., preferably from about 125 to about 250° C., in the presence of a catalytic amount of (a) a compound selected from the group consisting of
   i) lithium salts of aliphatic or aromatic mono- or dicarboxylic acids,
   ii) lithium salts of hydroxyl group containing compounds having from 1 to 3 hydroxyl groups per compound, wherein said hydroxyl groups are attached directly to an aromatic ring, and
   iii) lithium hydroxide; used in conjunction with
(b) an organic compound having at least one hydroxyl group.

According to the invention, from about 0.0001 to about 1 part of the lithium salt compound, or lithium hydroxide, should be used in conjunction with from about 0.01 to 10 parts of the organic compound which contains at least one hydroxyl group for 100 parts of isocyanate. The reaction can be run as either a batch or a continuous process. Reaction times vary between 1–240 minutes, and preferably from 2–120 minutes. It is preferred to use from about 0.001 to 0.01 parts of lithium salt or lithium hydroxide, and from about 0.05 to 4.0 parts of organic compound which contains hydroxyl groups per 100 parts of isocyanate.

Suitable lithium compounds for use in the present invention include both the monolithium and dilithium salts of aliphatic and aromatic carboxylic acids containing a total of from about 1 to 36 carbon atoms. Both the mono- or dicarboxylic acids are suitable for the process according to the invention. Examples of these lithium compounds include lithium formate, lithium salicylate, lithium acetate, lithium stearate, lithium propanate, lithium butyrate, lithium lactate, lithium laurate, lithium benzoate, lithium p-hydroxybenzoate, lithium 4-hydroxyphenylacetate, monolithium salt of oxalic acid, dilithium salt of oxalic acid, monolithium salt of glutaric acid, dilithium salt of glutaric acid, monolithium salt of isophthalic acid, dilithium salt of isophthalic acid, monolithium salt of phthalic acid, dilithium salt of phthalic acid, monolithium salt of terephthalic acid, and dilithium salt of terephthalic acid. Of these salts, lithium salicylate, lithium acetate, and lithium stearate are preferred.

The lithium compound may also be the lithium salt of a hydroxy group containing compound wherein the hydroxyl groups are directly attached to an aromatic ring. These compounds may contain from 1 to 3 hydroxyl groups each, and the aromatic ring contains a total of from 6 to 18 carbon atoms. Suitable compounds include lithium phenoxide, 4-methyl lithium phenoxide, 2-hydroxy lithium phenoxide, 3-hydroxy lithium phenoxide, 4-hydroxy lithium phenoxide, lithium 1-naphthoxide, lithium 2-naphthoxide, etc. Lithium salts of cresols, anthracenes, and phenanthracenes are also suitable trimerization catalysts. Theoretically, the lithium salts of substituted aromatic compounds are suitable provided the substituents do not deactivate the ring so that it is no longer an effective trimerization catalyst.

Lithium salts of carboxylic acids are readily obtained using standard preparative methods well known to one skilled in the art. Equation (1) represents a general preparative method.

$$R_1COOH + LiA \rightarrow R_1COO^-Li^+ + AH \qquad (1)$$

wherein:
$R_1$ represents hydrogen or an aliphatic or aromatic hydrocarbon chain of from 0–35 carbon atoms,
A represents a neutralized anion such as hydroxyl, hydride, alkoxide, etc.

The reactant LiA is used in an amount which is slightly less than molar equivalency, thereby ensuring that no residual reactant will remain in the products.

The lithium salts of hydroxyl group containing compounds wherein the hydroxyl groups are directly attached to an aromatic ring can be prepared by a typical acid base reaction, followed by the distillation of water, methanol, etc. However, the base must be stronger than the anion of the hydroxyl group of the aromatic compound. For example, lithium phenoxide can be prepared by reacting phenol with lithium hydroxide or lithium methoxide.

Suitable carboxylic acids for the preparation of the lithium salts (a)i) include those aliphatic and aromatic carboxylic acids having from about 1–36 carbon atoms. These acids may be either branched or straight chain, and either saturated or unsaturated. Both monocarboxylic acids and dicarboxylic acids are suitable. Some examples of these include formic acid, acetic acid, propionic acid, stearic acid, lactic acid, salicylic acid, lauric acid, glutaric acid, p-hydroxybenzoic acid, phthalic acid, isophthalic acid, and terephthalic acid. Theoretically, any compound having the carboxylic acid group would be suitable provided any additional substituents do not interfere with the formation of the salt.

Hydroxyl group containing compounds having at least one hydroxyl group attached directly to an aromatic ring which are suitable for the preparation of lithium salts (a)ii) include those aromatic alcohols containing from about 6 to 28 carbon atoms, and having from 1 to 3 hydroxyl groups present per aromatic ring. Examples of these aromatic compounds include phenol, m-cresol, resorcinol, hydroquinone, catechol, 1-naphthol, 2-naphthol, hydroxyanthracene, hydroxyphenanthrene, etc.

According to the present invention, these lithium compounds (a) are to be used in conjunction with a small amount of (b) an organic compound which contains hydroxyl groups. Generally these organic compounds contain from 1 to 4 hydroxyl groups and have about 1 to 18 carbon atoms. Suitable organic compounds include methanol, 1-ethanol, 1,2-ethanediol, 1-propanol, 2-propanol, 1-butanol, 2-butanol, isobutyl alcohol, n-amyl alcohol, sec-amyl alcohol, tert-amyl alcohol, 1-methylbutyl alcohol, 1-ethyl-1-propanol, n-octyl alcohol, 2-octyl alcohol, n-decyl alcohol, n-dodecyl alcohol, neopentylglycol, n-tetradecyl alcohol, n-hexadecyl alcohol, n-octadecyl alcohol, 1,3-propanediol, 1,4-butanediol, 1,3-butanediol, 2,3-butanediol, 3-methyl-2-butanol, 3,3-dimethyl-1-butanol, 2-ethyl-1,3-hexanediol, glycerol, 1,2,4-butanetriol, pentaerythritol, etc. It is preferred for these organic compounds to contain from 1 to 2 hydroxyl groups, such as a monoalcohol or a diol, and have from about 1 to 8 carbon atoms. Examples include methanol, 1-ethanol, 1-propanol, 2-propanol, 1-butanol, 2-butanol, n-amyl alcohol, 1-methylbutyl alcohol, 1-ethyl-1-propanol, n-octyl alcohol, 2-octyl alcohol, neopentylglycol, 1,3-propanediol, 1,4-butanediol, 1,3-butanediol, 2,3-butanediol, 2-ethyl-1,3-hexanediol, etc. It is most preferred to use those compounds which have 2 hydroxyl groups, and contain either 3 or 4 carbon atoms. 1,3-propanediol and 1,3-butanediol are among the most preferred organic compounds.

Suitable polyisocyanates to be trimerized according to the present invention, to yield polyisocyanates having an isocyanurate structure, include the known aliphatic, cycloaliphatic, araliphatic, aromatic, and heterocyclic polyisocyanates, and mixtures thereof. Examples of these polyisocyanates include those described by W. Siefen in Justus Liebigs Annalen der Chemie, 562, pages 7 to 236. More specifically, suitable polyisocyanates include, but are not limited to, 2,4-diisocyanatotoluene, 2,6-diisocyanatotoluene, diphenyl methane-4,4-diisocyanate, naphthylene 1,5-diisocyanate, hexamethylene-1,6 diisocyanate, 1-isocyanato-3,5,5-trimethyl-5-isocyanatomethyl-cyclohexane, 1,12-dodecane diisocyanate, cyclobutane-1,3-diisocyanate, cyclohexane-1,3-diisocyanate, cyclohexane-1,4-diisocyanate, 1-isocyanato-3,3,5-trimethyl-5-isocyanatomethyl cyclohexane (i.e. isophorone diisocyanate), 2,4- and/or 2,6-hexahydrotoluylene diisocyanate, hexahydro-1,3-phenylene diisocyanate, hexahydro-1,4-phenylene diisocyanate, perhydro-2,4'- and/or -4,4'diphenylmethane diisocyanate, 1,3- and/or 1,4-phenylene diisocyanate, diphenylmethane-2,4'-diisocyanate, naphthalene-1,5´-diisocyanate, triphenylmethane-4,4',4"-triisocyanate and polyphenyl polymethylene polyisocyanates obtained by phosgenating aniline/formaldehyde condensation products. Also suitable are polyisocyanate adducts containing urea, biuret, urethane, allophanate, uretdione, or carbodiimide groups or isocyanurate rings. Preferred polyisocyanates include aromatic and aliphatic isocyanates, with hexamethylene-1,6-diisocyanate, 2,4-diisocyanatotoluene, 2,6-diisocyanatotoluene, and diphenyl methane-4,4'-diisocyanate, and mixtures thereof, being particularly preferred.

EXAMPLES

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts are parts by weight.

Example 1

To a 250 ml 3-neck flask equipped with a condenser, thermometer, mechanical stirrer, and purged with dry nitrogen was added 100 grams of hexamethylene diisocyanate (HDI), 0.1 g. of 1,3-butanediol, and 0.002 g. of lithium salicylate. The reaction mixture was heated over a 4 minute period to 250° C. and held there for about 4 minutes. At the end of the time, it was cooled over a 3 minute period to about 40° C. and 0.01 g of benzoyl chloride was added. The resulting reaction mixture has a NCO content of 39.3%. The hexamethylene diisocyanate (HDI) monomer was removed by thin film evaporation to give a clear liquid having a viscosity of 7820 mPa.s at 25° C., and a NCO content of 20.4%.

Example 2

The same reaction was run as in Example 1, except that 0.006 g of lithium salicylate was used and no 1,3-butanediol was used. No trimerization was observed.

Example 3

The same reaction was ran as in Example 1, except that the lithium salicylate was dissolved in the 1,3-butanediol and this clear solution was added to the hexamethylene-1, 6-diisocyanate (HDI). The reaction mixture has a NCO content of 39.1% after heating.

The following formulations were also tested. All amounts are in parts by weight (pbw) unless otherwise indicated.
4. 100 hexamethylene-1,6-diisocyanate
   0.105 1,3-propanediol
   0.002 lithium salicylate
5. 100 hexamethylene-1,6-diisocyanate
   0.102 2-ethyl-1,3-hexanediol
   0.002 lithium salicylate
6. 100 hexamethylene-1,6-diisocyanate
   0.201 1,4-butanediol
   0.004 lithium salicylate
7. 100 hexamethylene-1,6-diisocyanate
   0.300 1,3-butanediol
   0.001 lithium salicylate 8. 100 hexamethylene-1,6-diisocyanate
   0.202 1,3-butanediol
   0.002 lithium salicylate
9. 100 hexamethylene-1,6-diisocyanate
   2.70 1,3-butanediol
   0.001 lithium salicylate
10. 100 hexamethylene-1,6-diisocyanate
    1.11 1-butanol
    0.004 lithium salicylate
11. 50 2,4-diisocyanatotoluene
    50 hexamethylene-1,6-diisocyanate
    0.200 1,3-butanediol
    0.002 lithium salicylate
12. 10 2,4-diisocyanatotoluene
    90 hexamethylene-1,6-diisocyanate
    0.200 1,3-butanediol
    0.004 lithium salicylate
13. 100 2,4-diisocyanatotoluene
    0.200 1,3-butanediol
    0.002 lithium salicylate
14. 60 diphenylmethane-4,4'-diisocyanate
    40 hexamethylene-1,6-diisocyanate
    0.200 1,3-butanediol
    0.002 lithium salicylate
15. 60 diphenylmethane-4,4'-diisocyanate
    40 hexamethylene-1,6-diisocyanate
    0.200 1,3-butanediol
    0.002 lithium salicylate
16. 100 diphenylmethane-4,4'-diisocyanate
    0.200 1,3-butanediol
    0.002 lithium salicylate
17. 100 hexamethylene-1,6-diisocyanate
    0.204 1,3-butanediol
    0.004 lithium acetate
18. 100 hexamethylene-1,6-diisocyanate
    0.201 1,3-butanediol
    0.005 lithium hydroxide
19. 100 hexamethylene-1,6-diisocyanate
    0.107 1,3-butanediol
    0.004 lithium stearate
20. 100 hexamethylene-1,6-diisocyanate
    0.103 1,3-butanediol
    0.002 lithium propanate
21. 100 hexamethylene-1,6-diisocyanate
    0.101 1,3-butanediol
    0.006 lithium lactate
22. 100 hexamethylene-1,6-diisocyanate
    0.202 1,3-butanediol
    0.006 lithium p-hydroxybenzoate
23. 100 hexamethylene-1,6-diisocyanate
    0.200 1,3-butanediol
    0.006 monolithium salt of isophthalic acid
24. 100 hexamethylene-1,6-diisocyanate
    0.103 1,3-butanediol
    0.006 monolithium salt of phthalic acid
25. 100 hexamethylene-1,6-diisocyanate
    0.201 1,3-butanediol
    0.006 dilithium salt of phthalic acid Table 1 presents the results for formulations 4–25. These experiments followed the same procedure as described in Example 1. Reaction temperatures and reaction times are listed in Table 1.

TABLE 1

| Formulation | Reaction Temp. °C. | Reaction Time, min. | Final % NCO |
| --- | --- | --- | --- |
| 4 | 250 | 4 | 37.7 |
| 5 | 250 | 4 | 46.0 |
| 6 | 160 | 20 | 28.7 |
| 7 | 220 | 5 | 40.0 |
| 8 | 125 | 155 | 39.5 |
| 9 | 125 | 154 | 41.7 |
| 10 | 125 | 51 | 37.5 |
| 11 | 125 | 4 | 40.3 |
| 12 | 125 | 37 | 40.5 |
| 13 | 125 | 65 | 40.6 |
| 14 | 125 | 2.25 | 30.5 |
| 15 | 175 | 41 | 29.9 |
| 16 | 200 | 60 | 21.8 |
| 17 | 250 | 2 | 38.6 |
| 18 | 250 | 4 | 34.2 |
| 19 | 250 | 4 | 39.1 |
| 20 | 250 | 4 | 40.3 |
| 21 | 250 | 4 | 31.1 |
| 22 | 250 | 4 | 41.9 |
| 23 | 250 | 4 | 32.1 |
| 24 | 250 | 4 | 41.0 |
| 25 | 250 | 4 | 41.3 |

Example 26

To a 250 ml. 3-neck flask equipped with a condenser, thermometer, mechanical stirrer, and purged with dry nitrogen, was added 100 parts hexamethylene-1,6-diisocyanate, 0.106 parts of 1,3-butanediol and 0.002 parts lithium salicylate. The reaction mixture was heated over a 5 minute period to 250° C. and held there for 8 minutes. At the end of this time, the mixture was cooled over a 3 minute period to about 50° C. and 0.01 parts of benzoyl chloride was added. The resulting mixture had an NCO content of 40.5%.

COMPARISON EXAMPLES

Example 27

The identical procedure as described in Example 26 was followed, except 0.002 parts of sodium salicylate was substituted for the lithium salicylate. The resulting mixture had an NCO content of 48.6%.

Example 28

The identical procedure as described in Example 26 was followed, except 0.002 parts of potassium salicylate was substituted for the lithium salicylate. The resulting mixture had an NCO content of 47.9%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a polyisocyanate having isocyanurate structure which comprises heating an organic polyisocyanate, or mixtures thereof, to a temperature of from about 100 to 300° C. in the presence of a catalytic amount of (a) a compound selected from the group consisting of i) lithium salts of aliphatic or aromatic monocarboxylic or dicarboxylic acids,
ii) lithium salts of hydroxyl group containing compounds having from 1 to 3 hydroxyl groups per compound, wherein said hydroxyl groups are directly attached to an aromatic ring, and
iii) lithium hydroxide; and (b) an organic compound containing at least one hydroxyl group for a period of from about 1 minute to about 240 minutes.

2. The process of claim 1 wherein (a) said compound is selected from the group consisting of lithium salicylate, lithium acetate, and lithium stearate.

3. The process of claim 1 wherein said temperature range is from 125 to 250° C.

4. The process of claim 1 wherein (b) said organic compound containing at least one hydroxyl group is selected from the group consisting of 1,3-propanediol and 1,3-butanediol.

5. The process of claim 1 wherein (a) said compound is lithium hydroxide.

6. The process of claim 1 wherein said organic polyisocyanate compound is selected from the group consisting of hexamethylene-1,6-diisocyanate, diphenylmethane-4,4-diisocyanate, toluylene diisocyanate, and mixtures thereof.

* * * * *